(12) United States Patent
Gleich et al.

(10) Patent No.: US 9,480,413 B2
(45) Date of Patent: *Nov. 1, 2016

(54) ARRANGEMENT AND METHOD FOR DETERMINING THE SPATIAL DISTRIBUTION OF MAGNETIC PARTICLES

(75) Inventors: Bernhard Gleich, Hamburg (DE); Juergen Weizenecker, Hamburg (DE); Nielsen Tim, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 201 days.

This patent is subject to a terminal disclaimer.

(21) Appl. No.: 12/696,911

(22) Filed: Jan. 29, 2010

(65) Prior Publication Data

US 2010/0249578 A1 Sep. 30, 2010

Related U.S. Application Data

(63) Continuation of application No. 11/721,565, filed as application No. PCT/IB2005/054248 on Dec. 14, 2005, now abandoned, which is a continuation-in-part of application No. 10/270,991, filed on Oct. 15, 2002, now Pat. No. 7,778,681.

(30) Foreign Application Priority Data

Oct. 19, 2001 (EP) .................................... 10151778
Dec. 22, 2004 (EP) .................................... 04106838

(51) Int. Cl.
*A61B 5/05* (2006.01)

(52) U.S. Cl.
CPC ................ *A61B 5/05* (2013.01); *A61B 5/0515* (2013.01)

(58) Field of Classification Search
CPC ........................... A61B 5/0515; A61B 5/055
USPC ......... 607/103; 335/299, 296; 600/422, 423, 600/10, 11, 12, 13, 14
See application file for complete search history.

(56) References Cited

U.S. PATENT DOCUMENTS

| | | | | |
|---|---|---|---|---|
| 5,353,795 A | * | 10/1994 | Souza et al. | 600/423 |
| 5,425,367 A | * | 6/1995 | Shapiro et al. | 600/424 |
| 5,728,079 A | | 3/1998 | Weber | |
| 5,964,705 A | * | 10/1999 | Truwit et al. | 600/423 |
| 6,154,110 A | * | 11/2000 | Takeshima | 335/299 |
| 6,216,026 B1 | * | 4/2001 | Kuhn et al. | 600/409 |

(Continued)

FOREIGN PATENT DOCUMENTS

| | | |
|---|---|---|
| DE | 10238853 A1 | 3/2004 |
| WO | 2004023153 A1 | 3/2004 |

(Continued)

*Primary Examiner* — Katherine Fernandez
*Assistant Examiner* — Farshad Negarestan

(57) ABSTRACT

A system for determining the spatial distribution of magnetic particles in an examination area. Magnetic field generator generates a spatially inhomogeneous gradient magnetic field with at least one region with a low field strength in which the magnetization of the particles is in a state of non-saturation, whereas they are in a state of saturation in the remaining region. By an arrangement to shift the area with a low field strength within the examination area, a change in the magnetization of the magnetic particles is brought about which can be detected from outside by a detector. At least one of the magnetic field generator, the arrangement and the detector are arranged at least partially on a medical instrument.

18 Claims, 2 Drawing Sheets

(56) References Cited

U.S. PATENT DOCUMENTS

| | | | |
|---|---|---|---|
| 6,236,205 B1* | 5/2001 | Ludeke et al. | 324/318 |
| 6,246,896 B1* | 6/2001 | Dumoulin et al. | 600/411 |
| 6,470,220 B1* | 10/2002 | Kraus et al. | 607/103 |
| 6,512,941 B1* | 1/2003 | Weiss et al. | 600/410 |
| 7,778,681 B2* | 8/2010 | Gleich | A61B 5/0515 324/300 |
| 2003/0052785 A1* | 3/2003 | Gisselberg et al. | 340/572.8 |
| 2003/0085703 A1 | 5/2003 | Gleich | |
| 2003/0135110 A1* | 7/2003 | Leussler | 600/422 |
| 2004/0127788 A1 | 7/2004 | Arata | |
| 2004/0158144 A1 | 8/2004 | Keren et al. | |

FOREIGN PATENT DOCUMENTS

| | | |
|---|---|---|
| WO | 2004091721 A1 | 10/2004 |
| WO | 2006067664 A2 | 6/2006 |

* cited by examiner

ARRANGEMENT AND METHOD FOR DETERMINING THE SPATIAL DISTRIBUTION OF MAGNETIC PARTICLES

This application is a continuation of prior U.S. patent application Ser. No. 11/721,565, filed Jun. 13, 2007, which was the National Stage of International Application No. PCT/IB2005/054248, filed Dec. 14, 2005, which claims the benefit of European Patent Application (EPO) No. 04106838.8, filed Dec. 22, 2004, which is a continuation-in-part of prior U.S. patent application Ser. No. 10/270,991, filed Oct. 15, 2002, which claims the benefit of German Patent Application No. 10151778.5, filed Oct. 19, 2001.

The invention relates to an arrangement for determining the spatial distribution of magnetic particles in an examination area using medical instruments and also to a method of determining the distribution. Furthermore, the invention also relates to medical instruments and to the use thereof in the abovementioned arrangement.

Such an arrangement and such a method are already known from DE10151778. In the method described therein, a spatially inhomogeneous magnetic field is generated, having at least one region with a low field strength, in which the magnetization of the particles is in a state of non-saturation, whereas they are in a state of saturation in the remaining region. By shifting the region with a low field strength within the examination area, a change in magnetization is brought about which can be detected from outside and contains information about the spatial distribution of the magnetic particles in the examination area. An arrangement for carrying out the method is also disclosed. The examination area is surrounded by a few coil arrangements, by means of which the inhomogeneous magnetic field is generated, the shift in the magnetic field regions is brought about and signals are detected. The signals are then evaluated.

It is an object of the invention to develop an improved arrangement.

This object is achieved as claimed in claim 1 by an arrangement for determining the spatial distribution of magnetic particles in an examination area, comprising a) magnetic field means for generating a magnetic field with a spatial course of the magnetic field strength such that there is in the examination area a first part-region with a low magnetic field strength and a second part-region with a higher magnetic field strength, b) change means for changing the spatial position of the two part-regions in the examination area, so that the magnetization of the particles changes locally, c) detection means for detecting signals which depend on the magnetization in the examination area that is affected by the change in spatial position, d) evaluation means for evaluating the signals in order to obtain information about the spatial distribution of the magnetic particles in the examination area, wherein the magnetic field means or the change means or the detection means or a combination of these means are arranged at least partially on a medical instrument.

With regard to the description of the invention, reference will be made to the following documents by the same Applicant, which are hereby fully incorporated by way of reference into the present text:

Ax1: German patent application DE10151778A1 bearing the title "Verfahren zur Ermittlung der räumlichen Verteilung magnetischer Partikel", Ax2: European patent application bearing the application number EP03101014.3 and the title "Verfahren and Gerät zur Beeinflussung magnetischer Partikel", Ax3: German patent application DE10238853A1 bearing the title "Verfahren zur lokalen Erwärmung mit magnetischen Partikeln".

The magnetic field means, change means and detection means and the modes of action thereof are described in general in documents Ax1 and Ax2, so that these means will be discussed here only with regard to the present invention. For further details regarding said means, reference should be made to the aforementioned documents.

As is known from the aforementioned documents, a gradient magnetic field having a first part-region which is for example a spatially coherent region is formed by the magnetic field means. In this part-region, the magnetic field is so weak that the magnetization of the particles differs to a greater or lesser extent from the external magnetic field, that is to say is not saturated. In the second part-region (that is to say in the rest of the examination area outside the first part or in that region which surrounds the first part-region), the magnetic field is strong enough to keep the particles in a state of saturation.

According to document Ax1, the magnetic field means consist for example of a Maxwell coil arrangement, of a coil and a permanent magnet, or of two permanent magnets opposite one another with identically poled ends. In addition, coil arrangements are also known from the document Ax2 in which the examination area does not lie within the magnetic field means but rather next to them. In all these arrangements, an inhomogeneous magnetic field or a gradient magnetic field is produced, in which a first part-region is formed which has a lower magnetic field strength or no magnetic field strength at all compared to its surroundings. Such a magnetic field is shown for example in documents Ax1 to Ax3, for instance in FIG. 2 in document Ax1.

According to the invention, the magnetic field means may be arranged at least partially on a medical instrument. As a result, it is possible to place the region with a low magnetic field strength in the vicinity of the medical instrument, in order to determine the distribution of the magnetic particles in the vicinity of the medical instrument. As a result, a higher gradient of the magnetic field is produced in the vicinity of the region with a low field strength, and this results in an improved resolution. Moreover, when the medical instrument is moved, the position of the region with a low field strength will not move or will hardly move with respect to the medical instrument, so that the region with a low magnetic field strength essentially follows the movement of the medical instrument. As a result, the distribution of the magnetic particles can always be determined in the vicinity of the medical instrument.

In the known arrangements from documents Ax1 to Ax3, the position of the region with a low magnetic field strength is predefined by the corresponding magnetic field means in the basic state, that is to say without any action by the change means. If the examination object (e.g. the patient) moves or shifts relative to the examination area during the examination, only a distorted or even completely incorrect assignment of the various positions of the region with a low field strength to the corresponding regions of the patient is possible. As a result, movement artifacts arise when determining the spatial distribution of the magnetic particles, as is also known for example from nuclear spin tomography. These movement artifacts can be reduced or avoided by at least partially arranging the magnetic field means on the medical instrument.

If the magnetic field means consist for example of a Maxwell coil arrangement, one of the two coils may be arranged on the medical instrument. If the magnetic field means include at least one permanent magnet, this may be arranged on the medical instrument as claimed in claim 2. The arrangement of a permanent magnet on the medical instrument is usually simple to achieve. In particular, unlike a coil, there is no need for any power supply or for lines to be guided out of the medical instrument. The embodiment as claimed in claim 3 corresponds to a similar arrangement, as disclosed in document Ax2. If the magnetic field means consist only of the components described therein, the magnetic field means may be arranged not just partially but rather completely on the medical instrument. As a result, the components surrounding the examination area are reduced.

As shown by way of example, magnetic field means may in general consist of one or more components. Therefore, in this connection, a partial arrangement of the magnetic field means on the medical instrument means that at least one component of the magnetic field means is arranged on the medical instrument.

The change in spatial position of the two part-regions may be brought about by means of various change means, as discussed for example in documents Ax1 or Ax2. On the one hand, coil arrangements of the magnetic field means may be used for this purpose if they are operated with an AC current in addition to a DC current. On the other hand, separate change means may also be used, for example by using a dedicated coil arrangement to generate a temporally variable magnetic field which is superposed on the gradient magnetic field. According to the invention, at least one such coil arrangement may be arranged on the medical instrument. As a result, during a periodic change in the position of the two part-regions, a much higher frequency can be used than in the known arrangements. This is because, in the arrangement of the change means which is known from the documents Ax1 to Ax3, the temporally variable magnetic fields are applied to a relatively large area of the examination object (patient). Possible heating of the examination object depends approximately on the product of amplitude and frequency of the temporally variable magnetic field. By arranging change means on the medical instrument, temporally variable magnetic fields are applied only locally in the vicinity of the medical instrument. As a result, the overall and local heating of the examination object is considerably reduced.

As shown by way of example, the change means may in general also consist of one or more components. In this connection, therefore, a partial arrangement of the change means on the medical instrument means that at least one component of the change means is arranged on the medical instrument.

If coil arrangements are at least partially used in the change means, these are operated with high frequencies, depending on the operating mode. The coil arrangements may heat up on account of the electrical resistance. Such a heating beyond a specific level may be undesirable in the case of a coil arrangement arranged on the medical instrument. The heating of a coil operated with high frequencies can be reduced as claimed in claim 4. As is known, the current flowing through the windings or the number of windings of the coil can be reduced by using a core, as a result of which the heating is reduced. The heat losses caused by the magnetic reversal in the core are minimized by its soft-magnetic properties, particularly if it has a magnetization characteristic which is as linear as possible within the range of the magnetic field strengths acting thereon.

According to documents Ax1 and Ax2, the signals coming from the magnetic particles can be detected by at least one coil or coil arrangement as detection means. According to the invention, this coil or coil arrangement may be arranged on the medical instrument. As a result, the signals can be detected with a considerably improved signal-to-noise ratio if the region with a low magnetic field strength is located in or is shifted into the vicinity of the detection means. As claimed in claim 5, use may also be made of a number of coils or coil arrangements having different directions of action. By way of example, as is known, a flat conductor loop can detect signals particularly well if the changing magnetic field stands vertical on the surface formed by the conductor loop. A direction of action of a coil or coil arrangement is therefore to be understood as meaning that direction in which a changing magnetic field acts on the coil or coil arrangement, with regard to maximum signal detection.

As shown by way of example, the detection means may in general also consist of one or more components. In this connection, therefore, a partial arrangement of the detection means on the medical instrument means that at least one component of the detection means is arranged on the medical instrument.

Within the context of this invention, a medical instrument is to be understood as meaning any article which can be used by a doctor or other staff for medical purposes, for example examinations or treatments. On the one hand, this is to be understood as meaning articles which are passed over the object to be examined and are placed on the patient's skin for example in the form of a scanning head. This term also includes scanning heads for example. Using such medical instruments, it is then possible to create images for example of blood vessels below the skin, using the invention and the methods described in documents Ax1 and Ax2. On account of the laws of physics, it is expected that signals worthy of evaluation can be generated and detected only up to a certain penetration depth in the examination object. If coils are used as magnetic field means, this penetration depth is proportional for example to the central area of these coils.

Furthermore, as claimed in claim 6, invasive medical instruments such as instruments for minimally invasive operations or a catheter as claimed in claim 7 also fall under the term "medical instrument". This term is also to be understood as meaning probes which can be inserted into the gullet, stomach, intestine, ear or other points of the human or animal body. This list is given by way of non-limiting example.

In order to be able to determine its position more easily, a marker is arranged on the medical instrument as claimed in claim 8. Such markers are disclosed in the document Ax4 bearing the title "Markers for position determination using magnetic methods", which was filed as a patent application with the European Patent Office on the same day and by the same Applicant as the present invention. Said patent application is hereby fully incorporated by way of reference.

By modifying the change means, the arrangement as claimed in claim 9 can also be used to implement a local hyperthermia, as disclosed in document Ax3.

As claimed in claims 10 to 13, use may be made of known medical instruments comprising coils, such as catheters from the field of nuclear spin tomography for example.

The method as claimed in claim 14 is based on the methods disclosed in documents Ax1, Ax2 and Ax3.

The invention will be further described with reference to examples of embodiments shown in the drawings to which, however, the invention is not restricted. The medical instrument described here is a catheter, although in principle other medical instruments may be used instead.

Figure 1:
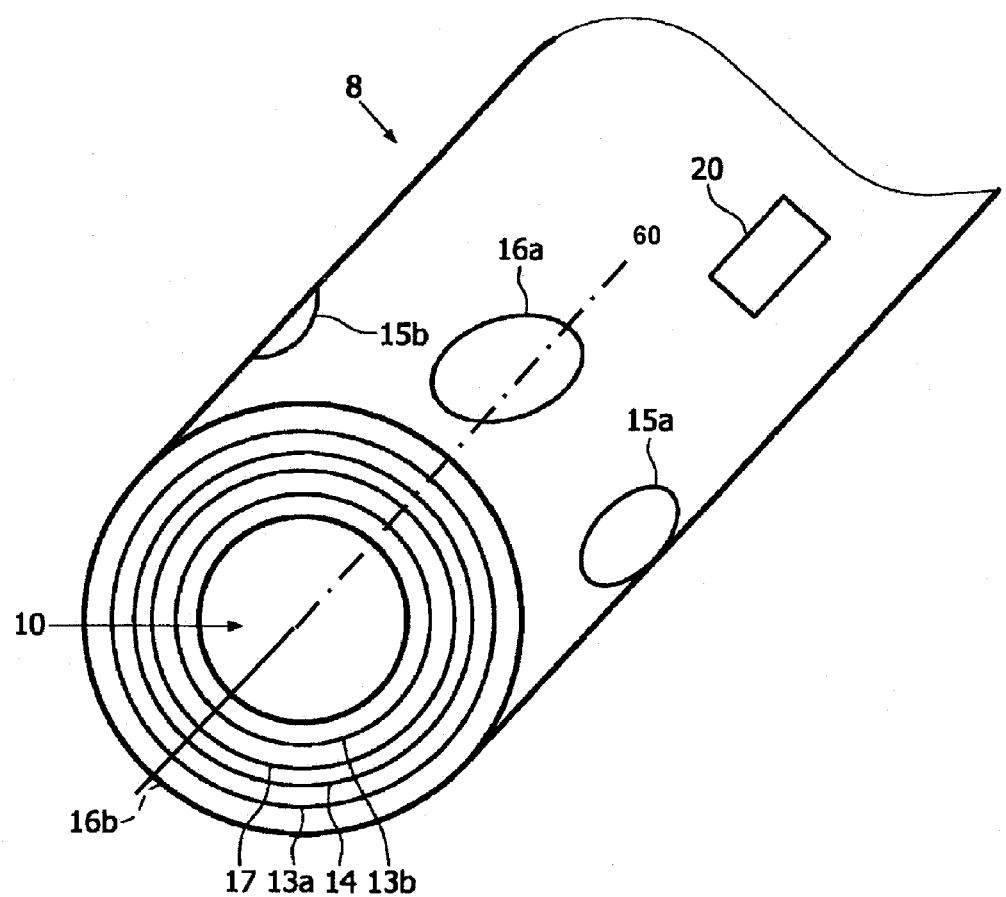
FIG. 1 shows a first catheter according to the invention.

FIG. 1 schematically shows the tip of a catheter 8. As is known, a catheter forms a thin hose-like line, through the interior of which for example a guidewire runs or liquids (such as contrast agents) are passed to the catheter tip and can exit through the opening 10.

In order to obtain information about the spatial distribution of magnetic particles in the examination object (here the patient) which are located in the vicinity of the catheter, coils and coil pairs are located on the catheter 8, the magnetic fields of which also pass through a region in front of the catheter tip. The coils mentioned below are shown only schematically as circles, so that the supply lines for example are not shown for the sake of better clarity. A first coil pair comprises the two windings 13a and 13b which surround one another coaxially and during operation are flowed through by currents in opposite directions, a common axis 60 of which windings runs more or less along an axis of the catheter 8. The gradient magnetic field generated thereby is shown and described in FIGS. 2a and 2b of the document Ax2. The position of the field-free point or of the region with a low field strength is selected such that it is located in front of the opening 10 of the catheter 8. Starting from this field-free point, the strength of the magnetic field increases in all three spatial direction as the distance from the field-free point increases.

In order to position the field-free point on the common axis, various parameters of the arrangement may be changed. If the current intensity of the current flowing through the winding 13a is increased or the current intensity of the current flowing through the winding 13b is reduced, the field-free point is displaced in the direction of the catheter. If, on the other hand, the current intensity of the current flowing through the winding 13a is reduced or the current intensity of the current flowing through the winding 13b is increased, the field-free point is displaced in the opposite direction. Moreover, the position, in particular the starting position, of the field-free point can be affected by changing the diameter of the windings 13a and 13b. Furthermore, it must be ensured by virtue of the dimensioning of the coil arrangement that the spatial size of the region with a higher field strength is sufficiently large. This means that, in this region, there should be magnetic particles whose signals could in principle be detected by the detection means described below but which in fact do not generate any signal and therefore are kept in a state of magnetic saturation. If the magnetic particles are far away from the detection means such that their signals are detected only weakly or not at all by the detection means, they moreover need no longer lie in the region with a higher magnetic field strength.

The size of the region with a low field strength (shown at reference 301 in FIG. 2b of document Ax2) which determines the spatial resolution of the device depends on the one hand on the strength of the gradient of the gradient magnetic field and on the other hand on the size of the magnetic field required for saturation. For deeper consideration, reference should be made to documents Ax1 and Ax2.

If one or more further magnetic fields are superposed on the gradient magnetic field in the zone of action, the field-free point or the region with a low field strength is then displaced along this superposed magnetic field, wherein the size of the displacement increases with the strength of the superposed magnetic fields. The superposed magnetic fields have different directions and may be temporally variable.

In order to generate these temporally variable magnetic fields for any direction in space, three further coil arrangements are provided as change means. A coil 14 generates a magnetic field which runs in the direction of the coil axis of the coil pair 13a, 13b. In principle, the effect that can be achieved by means of this coil pair can also be achieved by superposing currents of the same direction on the currents of opposite direction in the coil pair 13a, 13b, as a result of which the current decreases in one coil pair and increases in the other coil pair. However, it may be desirable if the temporally constant gradient magnetic field and the temporally variable vertical magnetic field are generated by separate coil pairs.

In order to generate magnetic fields which run spatially perpendicular to the common axis of the coils 13a and 13b and/or perpendicular to the catheter axis, two further coils pairs are provided, comprising the windings 15a, 15b and 16a, 16b. The winding 16b is not shown since it is arranged on the underside of the catheter, which is not visible. The windings 15a and 15b and the windings 16a and 16b are respectively arranged in an identical manner on the outer surface of the catheter 8 and lie opposite one another. The common axis of the coil pair comprising the windings 15a and 15b is perpendicular to the common axis of the coil pair 16a and 16b and the two axes of the coil pairs are in each case perpendicular to the axis of the catheter 8. During operation, a magnetic field forms between the two windings of a coil pair, the field lines of which magnetic field run on the one hand almost in a straight line through the catheter 8. On the other hand, they run in a curved manner around the catheter 8, wherein they also pass through the field-free point or the region with a low field strength in front of the catheter tip 8 with a component perpendicular to the catheter axis.

The shape of the windings may also be different in order to optimize the respective curved magnetic field. It is also conceivable for the reasons mentioned above to arrange a soft-magnetic core (not shown) inside the respective coils.

Finally, FIG. 1 shows a further coil 17 which serves to detect signals generated in the zone of action. In principle, any of the field-generating coil pairs 13 to 16 could also be used for this purpose. However, when use is made of a special coil, a more favorable signal-to-noise-ratio is obtained, particularly if a number of receiving coils (not shown) are used. In addition, the coil may be arranged and connected in such a way that it is decoupled from the other coils. If, for example, three receiving coils are fitted on the catheter, their directions of action may lie at an angle of 90° with respect to one another. As a result, signals are detected from all directions around the catheter tip. In addition, it is also possible to fit other external receiving coils (not shown) next to the examination object.

By virtue of the design of the catheter shown in FIG. 1, the position of the region with a low magnetic field strength relates to the catheter and no longer to the examination area or to the external components as described in documents Ax1 and Ax1 [sic]. In the basic state, therefore, the position of the region with a low field strength changes within the examination object only when there is a relative movement between catheter and examination object. If, during the time of signal detection, the catheter is stationary with respect to the region of the patient from which the signals are to be detected, the patient can move without this giving rise to movement artifacts. If images of the inner wall of an artery or of a coronary vessel are to be created by means of the catheter, for example, it is expected that even the complex movement of the heart will not lead or will lead only slightly to movement artifacts.

It is also possible, depending on the application, not to fit all of the coils shown in FIG. 1 to the catheter 8. By way of example, the coils 14, 15a, 15b, 16a and 16b may be omitted if external coils as described in Ax1 and Ax2 are used to shift the region with a low field strength.

In respect of the changing of the region with a low field strength, the detection of the resulting signals and the evaluation of said signals, reference should be made to documents Ax1 and Ax2. In addition, heating of magnetic particles is also possible, as described in document Ax3. Heating takes place here in the vicinity of the tip of the catheter. Prior to heating, the region to be heated can be displayed by means of the above-described method and a user can define the region to be heated.

In the catheter 8, it is also possible, by virtue of a different design and arrangement of the magnetic field means, to define the position of the field-free point or of the region with a low field strength so that it is not in front of but rather next to the tip of the catheter 8. This is useful for example when images of regions which are mainly located next to the catheter 8 are to be created. The coils or coil arrangements shown in detail in FIG. 1 may then possibly have different shapes or be oriented differently and as a result be arranged differently on the catheter 8. However, their function does not change.

Figure 2:
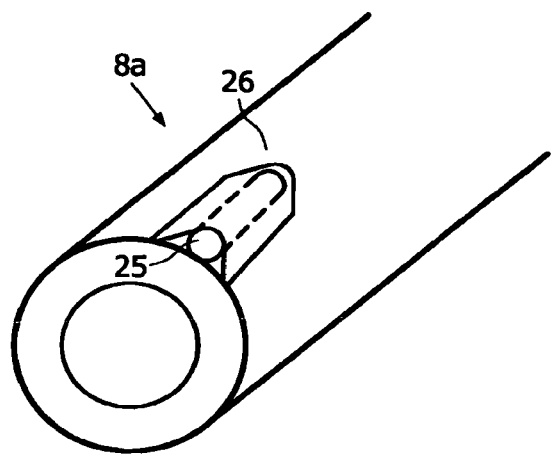
FIG. 2 shows a second catheter according to the invention.
Figure 3:
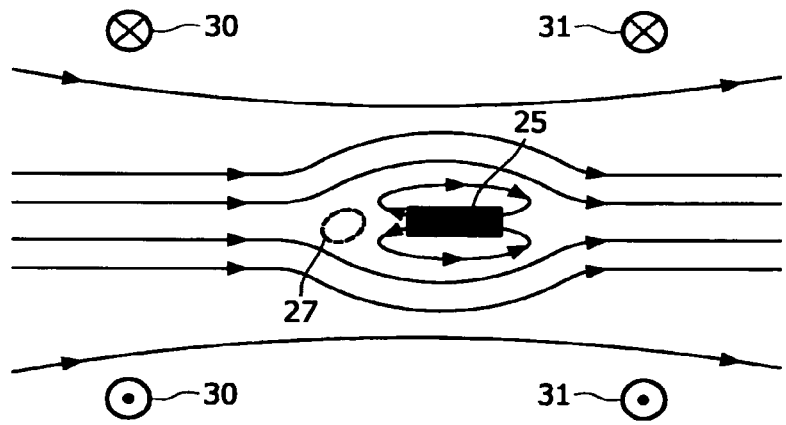
FIG. 3 shows the course of a first gradient magnetic field.

FIG. 2 shows a catheter 8a which essentially corresponds to the catheter 8 of FIG. 1. With the exception of the coils 13a and 13b, the catheter 8a contains all the components of the catheter 8, but these are not shown for the sake of clarity. In order to generate the gradient magnetic field, a bar-shaped permanent magnet 25 is fitted on the catheter 8a by a clip 26, one of the poles of said magnet lying at the end of the tip of the catheter 8a. When an external magnetic field whose field lines run more or less parallel to the axis of the catheter acts on said catheter, the field line course shown schematically in FIG. 3 is obtained. In FIG. 3, the external magnetic field is generated by a coil pair comprising the coils 30 and 31, wherein the coils 30 and 31 are arranged for example around the examination object. Instead of the catheter 8a, only the permanent magnet 25 is shown here. The left end of the permanent magnet 25 in FIG. 3 corresponds to the end of the permanent magnet 25 which faces the tip of the catheter as can be seen in FIG. 2.

By virtue of superposition with the magnetic field of the permanent magnet 25, a region 27 with a low magnetic field strength is obtained in front of the tip of the catheter 8a. If the catheter 8a with the permanent magnet 25 is displaced within the virtually homogeneous region of the external magnetic field, the region 27 accordingly moves therewith, without changing its position with respect to the catheter. The displacement of the region 27 and the detection of signals take place in the same manner as described for the catheter 8.

Compared to the catheter 8, the catheter 8a has fewer components. However, the region 27 is displaced with respect to the catheter 8a when the catheter 8a or the permanent magnet 25 rotates with respect to the illustrated position in such a way that the field lines of the external magnetic field no longer run parallel to the axis of the permanent magnet 25 or catheter 8a. This shift in position can be compensated for example by corresponding activation of the other coils or can be taken into account during signal evaluation. Another possibility is to likewise change the direction of the external magnetic field in a manner corresponding to the rotation of the permanent magnet 25. To this end, for example, further external magnetic fields with different directions may be superposed on the external magnetic field. The direction in which the catheter 8a or the permanent magnet 25 rotates may for example be determined by three orthogonal receiving coils arranged next to the examination object.

Figure 4:
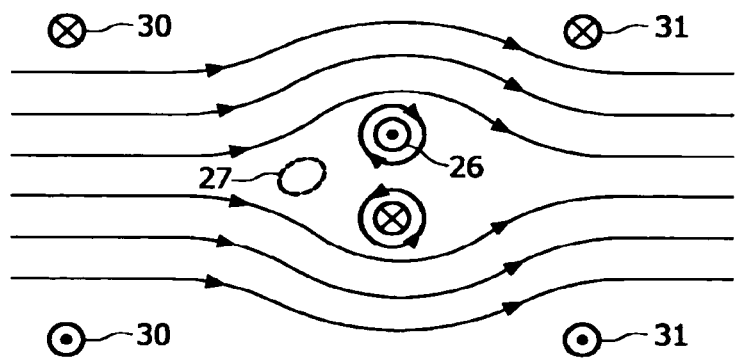
FIG. 4 shows the course of a second gradient magnetic field.

As an alternative to the illustrated bar-shaped permanent magnet 25, use may also be made of a ring-shaped permanent magnet which surrounds the tip of the catheter 8a or is embedded therein. Instead of a permanent magnet, use may in general also be made of a coil 26, wherein the course of the field lines shown in FIG. 4 is obtained.

The catheter 8 shown in FIG. 1 furthermore has a marker 20. Such markers and their function are described in detail for example in document Ax4, so that no further details are given at this point. If use is made of a marker which itself has magnetic properties (since it contains magnetic particles for example), it interferes with the other components arranged on the catheter 8. This is because on the one hand it distorts the gradient magnetic field and on the other hand it possibly also generates harmonic frequencies of the basic frequency, by means of which the region with a low field strength is shifted into its vicinity. The marker 20 should therefore be arranged at a sufficiently large distance from these components. Alternatively, the marker may also be configured such that its magnetic properties differ from the magnetic properties of the magnetic particles located in the surroundings of the catheter 8. Such differences may lie for example in the course of the magnetization curve (steepness, hysteresis). The signal coming from the marker then has a different spectral composition from the signals coming from the magnetic particles. In the case of a very large hysteresis, the signal coming from the marker may even almost disappear.

In the catheter 8 shown in FIG. 1, the marker may also be used to calibrate the position of the region with a low field strength with respect to the currents flowing through the coils. This is possible since the geometric position of the marker with respect to the coils is known. If the magnetic field means, in this case the coil pair comprising the two windings 13a and 13b, are not fitted on the catheter, the position of the catheter in the examination area can be determined by means of the marker.

The invention claimed is:

1. A system for determining spatial distribution of magnetic particles in an examination area, the system comprising:
   an invasive medical instrument;
   a first coil device having first and second coils configured to generate a magnetic field in the examination area including a first region with a low magnetic field strength and a second region with a higher magnetic field strength;
   a second coil device configured to generate a spatially variable magnetic field in the examination area to change a spatial position of the first region responsive to movement of the invasive medical instrument thereby changing a magnetization of the magnetic particles local to the invasive medical instrument with the first region substantially following movement of the invasive medical instrument and substantially maintaining a position of the first region with respect to the invasive medical instrument;

a third coil device configured to detect the change in the magnetization of the magnetic particles in the examination area affected by the change in the spatial position of the first region; and a processor configured to determine a spatial distribution of the magnetic particles in the examination area, wherein the spatial distribution is determined based on the detected change in magnetization of the magnetic particles, wherein at least one of the first, second and third coil devices are arranged on the invasive medical instrument.

2. The system as claimed in claim 1, wherein the first coil device is arranged on the invasive medical instrument and comprises at least one of a coil arrangement and a permanent magnet.

3. The system as claimed in claim 1, wherein the first coil device is arranged on the invasive medical instrument and comprises at least two coils arranged one inside another that during operation are flowed through by currents that flow respectively in an opposite direction in one of the at least two coils as compared to another one of the at least two coils.

4. The system as claimed in claim 1, wherein the second coil device is arranged on the invasive medical instrument and comprises a coil arrangement with a magnetic core.

5. The system as claimed in claim 1, wherein the third coil device is arranged on the invasive medical instrument and comprises a plurality of coils or coil arrangements, wherein directions of action of the plurality of coils or coil arrangements are at an angle to one another.

6. The system as claimed in claim 1, wherein the invasive medical instrument is a catheter having a tip and the at least one of the first, second and third coil devices are arranged on or in a vicinity of the catheter tip.

7. The system as claimed in claim 6, wherein the invasive medical instrument has an opening located at the tip and the second coil device is arranged on the invasive medical instrument and wherein the first region with the low magnetic field strength is located in front of the opening.

8. The system as claimed in claim 7, wherein the first coil device is arranged on the invasive medical instrument and comprises at least two coils arranged coaxially one inside another each having a common axis that runs substantially along an axis of the invasive medical instrument.

9. The system as claimed in claim 1, wherein the invasive medical instrument comprises a marker.

10. The system as claimed in claim 1, wherein the second coil device is further configured to change the spatial position of the first and second regions in a target area to heat up the target area.

11. The system as claimed in claim 1, wherein the at least one of the first, the second, and the third coil devices are configured for a medical purpose.

12. The system as claimed in claim 11, wherein the invasive medical instrument is a catheter.

13. The system as claimed in claim 1, wherein the invasive medical instrument is a catheter.

14. A method of determining the spatial distribution of magnetic particles in an examination area, the method comprising acts of:

introducing an invasive medical instrument including at least one of first, second and third coil devices into the examination area, wherein the first coil device generates a magnetic field in the examination area including a first region with a low magnetic field strength and a second region with a higher magnetic field strength;

moving the invasive medical instrument in the examination area;

generating a spatially variable magnetic field for changing a spatial position of the first region responsive to the movement of the invasive medical instrument thereby changing a magnetization of the magnetic particles local to the invasive medical instrument with the first region substantially following the movement of the invasive medical instrument and substantially maintaining a position of the first region with respect to the invasive medical instrument;

detecting the change in magnetization of the magnetic particles in the examination area affected by the change in the spatial position of the first region; and determining, by a processor, a spatial distribution of the magnetic particles in the examination area based on the detected change in magnetization of the magnetic particles.

15. A system for determining spatial distribution of magnetic particles in an examination area, the arrangement comprising:

an invasive medical instrument;

a first coil device having first and second coils configured to generate a magnetic field in the examination area including a low magnetic field strength region and a higher magnetic field strength region;

a second coil device configured to generate a spatially variable magnetic field in the examination area to change a spatial position of the low magnetic field strength region responsive to movement of the invasive medical instrument thereby changing a magnetization of the magnetic particles local to the invasive medical instrument with the low magnetic field strength region substantially following movement of the invasive medical instrument and substantially maintaining a position of the low magnetic field strength region with respect to the invasive medical instrument;

a third coil device configured to detect the change in the magnetization of the magnetic particles in the examination area affected by the change in the spatial position of the first region; and a processor configured to determine a spatial distribution of the magnetic particles in the examination area, wherein the spatial distribution is determined based on the detected change in magnetization of the magnetic particles, wherein at least one of the first, second and third coil devices are arranged on the invasive medical instrument.

16. The system as claimed in claim 15, wherein the invasive medical instrument is a catheter having a tip and at least one of the first, second and third coil devices are arranged on or in a vicinity of the catheter tip.

17. The system as claimed in claim 16, wherein the invasive medical instrument has an opening located at the tip and the second coil device is arranged on the invasive medical instrument and wherein the low magnetic field strength region is located in front of the opening.

18. The system as claimed in claim 17, wherein the first coil device is arranged on the invasive medical instrument and comprises at least two coils arranged coaxially one inside another each having a common axis that runs substantially along an axis of the invasive medical instrument.

* * * * *